United States Patent [19]

Brown

[11] 4,326,028
[45] Apr. 20, 1982

[54] ANTIBIOTIC TESTING VESSEL

[76] Inventor: Lewis R. Brown, 5 Hialeah Dr., Starkville, Miss. 39759

[21] Appl. No.: 185,746

[22] Filed: Sep. 10, 1980

[51] Int. Cl.³ .............................................. C12Q 1/18
[52] U.S. Cl. ........................................ 435/32; 435/30; 435/293; 435/298; 435/299
[58] Field of Search .................... 435/29, 30, 32, 33, 435/287, 292, 293, 294, 297, 298, 299, 300, 301

[56] References Cited

U.S. PATENT DOCUMENTS

| | | | |
|---|---|---|---|
| 2,533,089 | 12/1950 | Brewer et al. | 195/139 |
| 2,677,646 | 5/1954 | Lovell et al. | 435/297 X |
| 2,761,813 | 9/1956 | Goetz | 435/32 X |
| 2,923,669 | 2/1960 | Poitras | 195/163.5 |
| 3,616,265 | 10/1971 | Calabrese et al. | 435/293 X |
| 3,684,660 | 8/1972 | Kereluk et al. | 435/298 X |
| 3,741,877 | 6/1973 | Shaufus et al. | 435/297 X |
| 3,776,818 | 12/1973 | Khan | 435/32 X |
| 3,886,047 | 5/1975 | Billups, Jr. | 435/298 |
| 4,204,045 | 5/1980 | Kjellander et al. | 435/301 |
| 4,246,339 | 1/1981 | Cole et al. | 435/287 X |

*Primary Examiner*—Robert J. Warden
*Attorney, Agent, or Firm*—Ferris M. Stout

[57] ABSTRACT

A perforated gel-supporting structure with a temporary seal attached to it divides a cylindrical dish into cylindrical compartments A and B. Microorganisms are grown on agar poured into compartment A. The dish is inverted, the seal removed, and a second nutrient medium is poured into compartment B. Antibiotic substances produced by the microorganisms diffuse through the agar and inhibit growth of pathogens which have been inoculated into compartment B.

4 Claims, 3 Drawing Figures

ANTIBIOTIC TESTING VESSEL

DEFINITIONS

In this specification, these words have these specific meanings:

An antibiotic is a chemical substance produced by microorganisms which has the capacity, in dilute solution, to inhibit the growth of or to destroy bacteria and other microorganisms.

A microorganism is a minute living organism, usually microscopic in size.

A pathogen is a disease-producing microorganism.

BACKGROUND

Ever since the discovery by Sir Alexander Fleming that the fungus *Penicillium notatum* produced a substance inhibitory to the growth of the human pathogen, *Staphylococcus aureus*, the reseach for antibiotics has consumed vast amounts of time and money.

Thousands of antibiotics produced by microorganisms have been identified. Most of them, unfortunately, are toxic not only to pathogens, but also to the human hosts that harbor the pathogens, and only a few dozen antibiotics have found their way into medical practice. The search continues for new antibiotics which will control particular pathogens, especially those which are resistant to known antibiotics. There is also a need for antibiotics which are effective against animal and even plant pathogens.

There are several classical methods for searching for and isolating microorganisms which produce antibiotics. In one method, soil is sprinkled onto the surface of a solid nutrient medium, such as gelled agar, in a petri dish and individual colonies of microorganisms are encouraged to grow. Circular areas clear of other growth around some of the colonies indicate that an antibiotic is inhibiting the growth of neighboring colonies. This is how antibiotic-producing colonies are identified. Each such colony must then be tested for its ability to inhibit the pathogen against which an antibiotic is sought. To test a colony, one may remove a plug of agar containing the active colony and place the plug on a second plate of nutrient medium which has been "seeded", or uniformly inoculated with the pathogen against which one seeks an antibiotic. A clear area surrounding the plug indicates that the antibiotic produced is effective against the pathogen.

This method has a shortcoming: For the antibiotic to be evident in the first place, it must be effective against neighboring bacteria cultured from, and present in, the original soil sample. Each antibiotic has its own particular spectrum of organisms against which it is effective. If an organism present in the soil sample produces an antibiotic effective against the pathogen, but not against neighboring soil-derived colonies, its effectiveness will be undetected. If an antibiotic producer is a slow grower, its neighbor may grow rapidly enough to overwhelm and mask the antibiotic effect. Most pathogens, being obligate parasites and many times fastidious, are often vulnerable to weak antibiotics, the very antibiotics least likely to be toxic to the pathogen host. Yet, it is the weak antibiotics which are most likely to be undetected by this method, for the reasons discussed.

A further shortcoming of this method is the time and space requirement for two-step culturing, first against neighboring colonies, and then against the pathogen. When thousands of tests are to be made these constraints are seriously limiting.

In another test method, an unknown sample of microorganisms, as for example from the soil, is grown directly upon a nutrient medium which has been pre-seeded with a pathogen, and clear areas are sought in the medium, indicating antibiotic action against the pathogen directly. In this case, it is required that the new antibiotic producer thrive in the same environment as the pathogen - at the same temperature, pH, aerobicity, and so forth. Pathogens, however, frequently require exotic media and often require a special pH or redox potential which may not be acceptable to the culture of the very microorganisms which produce the sought-for antibiotic. There is, therefore, an even larger risk of passing up the most promising new candidate microorganisms. In this method, temperature is a major problem since most human pathogens require a temperature of 37° C. and most soil microorganisms grow best at about 25° C. Additionally, if the pathogen is a strict anaerobe (cannot grow in the presence of oxygen), aerobic antibiotic-producing organisms effective against the pathogen will not be found.

As indicated previously, soil is the source material for almost all antibiotic-producing organisms. The only practical way to find new antibiotics is to conduct massive soil screening programs. The methods described above, and with minor permutations thereof, have been employed since the search for antibiotic-producing microorganisms began. Many potentially valuable antibiotics have surely been missed in these screening procedures, since the procedures rely on the ability of the antibiotic-producing microorganism either to inhibit its neighbors, or to produce an antibiotic when cultured under conditions optimal for the growth of the pathogen, rather than optimal for the antibiotic-producing microorganism. Under these constraints, the cost of finding a new antibiotic-producing organism of potential value is becoming economically impractical. There is, then, an urgent need for an effective and efficient method for screening source materials (e.g. soils) for microorganisms capable of inhibiting specific pathogens.

This invention is a unique device and method for culturing microorganisms which fills this need. Two cultures, e.g. a pathogen and mixed soil microorganisms, are grown sequentially in the same vessel, each on its preferred medium. The two media in the vessel are disposed, sandwich-like, back-to-back. Antibiotics produced on one side of the media sandwich diffuse through it and inhibit growth (cause a clear area) on the pathogen side of the sandwich. Even though an antibiotic is too weak to inhibit neighbor colonies, it will inhibit the pathogen growing on the other side of the media sandwich. Even though an antibiotic producer grows more slowly than its neighbors, the antibiotic action on the pathogen is evident.

SUMMARY

Figure 1:
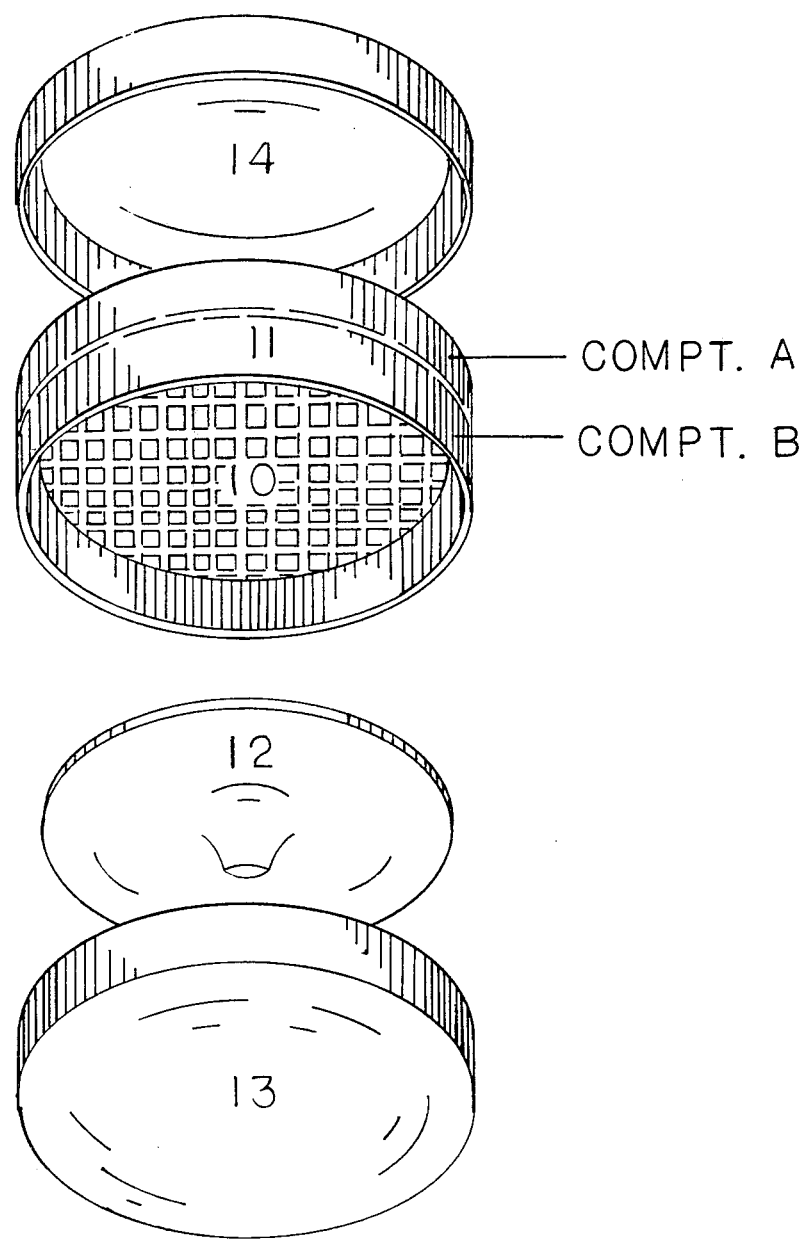
FIG. 1 is an exploded cross-sectional view of the Antibiotic Testing Vessel.

A porous support member perpendicular to the axis of the flat cylinder in which it is fastened divides a flat cylinder into two dish-like halves: An upper compartment A and a lower compartment B. The porous member is temporarily sealed by a removable plate on the compartment B side of it. Lids are provided for both sides of the cylinder.

A solid nutrient agar medium is melted, poured into compartment A, allowed to harden, and microorganisms to be tested are inoculated upon it and the plate incubated under a chosen set of environmental conditions. Alternatively, the microbial inoculum (e.g. soil) may be mixed with the melted and cooled nutrient medium, poured into compartment A, and allowed to harden.

After growth, the cylinder is inverted. The plate which seals the screen is removed; the porous support member prevents the gelled agar in compartment A from sagging.

A second medium, melted, cooled (but still liquid) and seeded with a pathogen, is poured into compartment B, where it gels. (The pathogen may be spread onto the surface of the medium in compartment B rather than incorporated into it.) The inoculated pathogen is cultured in an environment favorable to its proliferation. That is, such variables as pH, temperature, oxygen concentration, and the like are controlled optimally.

An antibiotic generated by a culture in compartment A will diffuse through the agar layer in which it is growing, through the porous member supporting the agar gel, and into the pathogen-containing agar in compartment B, causing a clear area therein, which may be readily observed.

PREFERRED EMBODIMENT

A preferred embodiment is illustrated schematically in the drawings.

In FIG. 1, 10 represents the porous support member which divides cylinder 11 into upper compartment A and lower compartment B. Seal 12, shown detached from the assembly, will snap into position to seal support member 10 and hold liquid agar poured into compartment A while it gels. 13 and 14 are lids which fit over the ends of the cylinder.

Figure 2A:
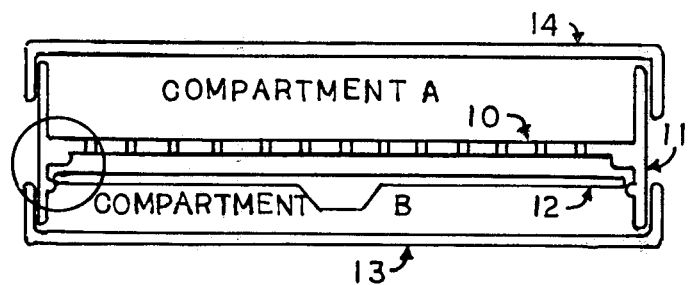
FIG. 2A is a schematic cross-sectional view of the Antibiotic Testing Vessel.
Figure 2B:
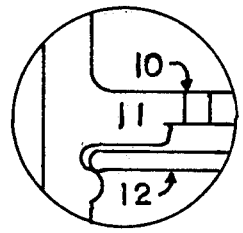
FIG. 2B is an enlarged view of a part of FIG. 2A.

FIG. 2A shows the Antibiotic Testing Vessel (ATV hereafter) assembled. [The insert in] FIG. 2B shows a construction for holding seal 12 in place against a shoulder to provide clearance between seal 12 and support member 10.

The sole purpose of support member 10 is to support the sheet of agar once it has gelled. The holes in the support member are as large, and the material between the holes is as thin, as is consistent with that purpose. Seal 12 must allow clearance between its surface and support member 10 to allow a continuous sheet of gel to form, so that support member 10 will become embedded in, and thereby support the body of the hardened gel when the seal is removed.

Preferably, the ATV is injection molded of inexpensive, transparent plastic, after which is gas sterilized and packaged in a sterile package.

Figure 3:
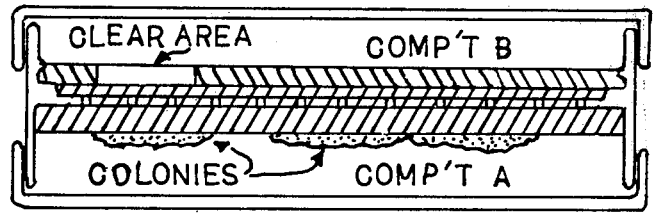
FIG. 3 is a schematic cross-sectional view of the Antibiotic Testing Vessel, showing bacterial cultures growing on a layer of agar in Compartment A, and a clear area in the seeded medium of Compartment B.

In FIG. 3, the ATV is shown assembled, with colonies growing in compartment A, one of which has produced an antibiotic, and a corresponding clear area above it in the medium of compartment B, in which a pathogen has been cultured.

EXPERIMENT 1

A fifty gram sample of soil is vigorously shaken with 100 ml of physiological saline and dilutions are prepared using the same solution. One ml of a 1/10,000 dilution of the soil suspension is added to melted nutrient agar which has been cooled to 47° C. After mixing, the still-liquid agar is poured into compartment A of an ATV and allowed to harden into an agar plate. A similar plate is prepared in a second ATV using Marine Agar. Plates are also prepared in a third and a fourth ATV from the same original soil suspension, but using a 1/1,000,000 dilution, and Tomato Juice Agar and Tryptic Soy Agar, respectively. Examination of the plates after incubation for 48 hours at 22° C. reveals that the microbial colonies which develop on the different media differ, as expected, in response to the different nutrients supplied in the different agar media.

The seal is removed from the bottom of each ATV, it is inverted, and a thin layer of melted and cooled nutrient agar, previously inoculated with a saline suspension of *Sarcina lutea,* is poured into compartment B. The agar is allowed to harden, and the ATV's are incubated a second time at 35° C. for 24 hours. Several clear areas in the *S. lutea* seeded agar indicate inhibition by antibiotics produced by the colonies in the agar of compartment A directly below the clear zones.

The antibiotic-producing cultures are isolated. Further tests indicate that different antibiotic-producing cultures develop in the different media used in the ATV's. Although the same soil sample was used in each of them.

This experiment shows that varying environmental conditions will cause various antibiotics to be produced from the same source of mixed microorganisms.

EXPERIMENT 2

A test similar to Experiment 1 is conducted using only Tryptic Soy Agar. Different ATV's are inoculated with the same soil slurry, and are incubated at different temperatures: 10° C., 20° C., 25° C., 30° C., 35° C., and 45° C. The types of colonies which develop at the different temperatures are similar, but some of the types which proliferate when incubated at 35° C. and 45° C. are absent on the plates incubated at 10° C. and 20° C.

*Sarcina lutea* is again employed as the test organism against which an antibiotic is sought, as in Experiment 1.

In this experiment colonial types produce clear zones of inhibition in the *S. lutea*-seeded agar. The clear zones are of greater diameter at the higher temperatures. This shows greater antibiotic production by this particular microorganism at the higher temperatures. The experiment shows how the ATV can be used to characterize optimal conditions for antibiotic production.

EXPERIMENT 3

In this experiment, one ATV of agar is seeded with soil as in Experiment 1 and incubated under anaerobic conditions. A second, similarly prepared ATV is incubated under aerobic conditions. Both ATV's are incubated at 22° C. A different flora develops on the two plates. Some types of colonies are present on both plates, while other types are present only on one or the other ATV.

As in Experiment 1, each ATV is inverted, the seal removed, and *S. lutea* is cultured in compartment B. The number and types of colonies inhibiting the *S. lutea* are different on the two ATV's. One antibiotic-producer is present only on the aerobic plate. Another producer is present only on the anaerobic plate.

This experiment shows the usefulness of the ATV in detecting antibiotic producers under different environmental conditions. To obtain the same information by conventional testing means would require a prohibitively complex procedure.

EXPERIMENT 4

To detect microorganisms capable of producing antibiotics effective against cancer cells, the procedure is as follows: The appropriate nutrient medium and microorganism inoculum is cultured in compartment A, as above. After growth of the microorganisms in compartment A has started, the plate is inverted, the seal is removed, and a semi-solid agar suspension of cancer cells is poured into compartment B. The cells are incubated under appropriate conditions, and are observed under a microscope for proliferation. Evidence of an antibiotic effective against the cancer cells will be evident by a paucity of cells, or evidence of inhibited proliferation of the cancer cells, in areas of the semi-solid gel directly above the antibiotic-producing organism.

EXPERIMENT 5

An agar medium is mixed with a sample of a waste water, the components of which might be useful; for example, a dairy waste. A solid agar plate of the mixture is prepared in Compartment A of an ATV, and is inoculated with a soil sample, as in Experiment 1.

After incubation, the plate is inverted and the seal removed. An agar medium, seeded with a microorganism which requires methionine for growth, is poured into compartment B and allowed to harden. After a second incubation under conditions optimal for the methionine-dependent microorganism, the plate is examined for colonies. Colonies of methionine-dependent microorganisms growing in compartment B indicate that colonies on the agar in compartment A directly beneath them produce methionine. The size of the colonies in compartment B is a measure of the quantity of methionine produced by the microorganisms in compartment A beneath them.

This experiment shows how the ATV is used to isolate microorganisms which can produce valuable, biologically useful chemicals other than antibiotics, using a specific substrate (in this case, dairy waste) as an energy source. The microorganism, once isolated, may be exposed to a mutagen in hopes of increasing its productivity, the improved mutants being isolated by the same ATV technique. Conventionally employed technology would entail multitudinous, expensive, and time-consuming chemical analysis to accomplish the same ends.

It will be clear to those skilled in the art of microbiology that the ATV can be used in these many other ways to detect and isolate microorganisms useful for many purposes. The terms and conditions used in the foregoing experiments and explanation are only exemplary of the invention, and are not to be construed as limiting the scope thereof, which is defined below in claims.

What is claimed is:

1. A vessel for testing the biological activity of substances produced by microorganisms cultured on agar which comprises
   a cylinder,
   a perforate support member attached on its periphery to the inner wall of the cylinder, for supporting a layer of hardened agar perpendicular to the axis of the cylinder, and
   sealing means removably attached to the inner wall of the cylinder adjacent the perforate support member for sealing the perforate support member while liquid agar poured onto it hardens.

2. A vessel for testing for the biological activity of substances produced by microorganisms cultured on a gel, the vessel comprising
   a cylinder, and
   a perforate support member attached on its periphery to the inner wall of the cylinder perpendicular to the axis of the cylinder, so as to divide the cylinder into two compartments.

3. A method of assaying for biologically active substances produced by microorganisms cultured on a gel which comprises the steps of
   providing a cylinder which has a perforate support member transversely separating the cylinder into a first compartment and a second compartment, the support member being sealed by a removable seal on the side of the second compartment,
   pouring a first melted nutrient gel medium into the first compartment of the cylinder and allowing the gel to harden, whereby the hardened gel is supported by the support member;
   inoculating the gel with one or more sample microorganisms;
   incubating the sample microorganisms;
   inverting the cylinder and removing the seal;
   pouring a second nutrient medium into the second compartment, whereby the second nutrient medium will be in contact with the cell-free side of the first nutrient medium;
   inoculating the second nutrient medium with a test microorganism;
   incubating the test microorganism in the second compartment, and
   observing the second nutrient medium for the development of areas which indicate biologically active substances produced by the sample microorganisms on the gel in the first compartment.

4. The method of claim 3 wherein the test microorganism is mixed with the second nutrient medium before it is poured into the second compartment.

* * * * *